(12) United States Patent
Pace et al.

(10) Patent No.: US 7,189,314 B1
(45) Date of Patent: Mar. 13, 2007

(54) METHOD AND APPARATUS FOR QUANTITATIVE ANALYSIS

(75) Inventors: Salvatore J. Pace, Ann Arbor, MI (US); James H. Youngblood, III, Bloomfield Hills, MI (US)

(73) Assignee: Sensicore, Inc., Ann Arbor, MI (US)

( * ) Notice: Subject to any disclaimer, the term of this patent is extended or adjusted under 35 U.S.C. 154(b) by 20 days.

(21) Appl. No.: 10/657,760

(22) Filed: Sep. 8, 2003
(Under 37 CFR 1.47)

Related U.S. Application Data

(60) Provisional application No. 60/408,806, filed on Sep. 6, 2002.

(51) Int. Cl.
*G01N 27/333* (2006.01)

(52) U.S. Cl. .................. 204/412; 204/416; 204/433

(58) Field of Classification Search ............... 204/412, 204/416, 422, 433; 205/778.5, 781.5, 787.5, 205/789
See application file for complete search history.

(56) References Cited

U.S. PATENT DOCUMENTS

| | | | | |
|---|---|---|---|---|
| 4,225,410 A | | 9/1980 | Pace | 204/195 |
| 4,454,007 A | | 6/1984 | Pace | 204/1 |
| 4,613,422 A | | 9/1986 | Lauks | 204/419 |
| 4,713,165 A | * | 12/1987 | Conover et al. | 204/403.05 |
| 4,743,954 A | | 5/1988 | Brown | 357/25 |
| H745 H | * | 2/1990 | Ishizuka et al. | 204/418 |
| 5,102,526 A | | 4/1992 | Brown et al. | 204/415 |
| 5,103,179 A | * | 4/1992 | Thomas et al. | 324/438 |
| 5,120,421 A | * | 6/1992 | Glass et al. | 204/406 |
| 5,200,051 A | | 4/1993 | Cozzette et al. | 204/403 |
| 5,284,568 A | | 2/1994 | Pace et al. | 204/403 |
| 5,330,634 A | * | 7/1994 | Wong et al. | 205/777.5 |
| 5,460,710 A | * | 10/1995 | Williams et al. | 205/780 |
| 5,483,164 A | | 1/1996 | Moss et al. | 324/425 |
| 5,554,272 A | * | 9/1996 | Benco et al. | 205/778 |
| 5,687,091 A | * | 11/1997 | Maung et al. | 700/266 |
| 5,795,996 A | * | 8/1998 | Chang et al. | 73/61.41 |
| 6,003,164 A | * | 12/1999 | Leaders | 4/507 |
| 6,635,683 B1 | * | 10/2003 | Taira et al. | 521/27 |
| 2003/0111424 A1 | * | 6/2003 | Rosen et al. | 210/747 |

FOREIGN PATENT DOCUMENTS

EP 0933635 A2 * 8/1999

(Continued)

OTHER PUBLICATIONS

JPO computer English language translation of Yasutaka et al. (JP 2001-153836 A).*

(Continued)

*Primary Examiner*—Alex Noguerola
(74) *Attorney, Agent, or Firm*—Marshall, Gerstein & Borun LLP

(57) ABSTRACT

A sensory apparatus including a substrate including a plurality of sensors to obtain an analyte profile, the sensors including an ion-selective sensor capable of measuring ion content and a chlorine sensor capable of measuring chlorine content, is disclosed. A method of generating an analyte profile, including measuring, directly or indirectly, properties including free chlorine concentration, pH, calcium ion concentration, carbonate ion concentration, and bicarbonate ion concentration, concurrently on a contiguous sample, is also disclosed.

18 Claims, 8 Drawing Sheets

FOREIGN PATENT DOCUMENTS

| | | | |
|---|---|---|---|
| GB | 2290617 A | * | 8/1994 |
| GB | 2368838 A | * | 5/2002 |
| JP | 09329577 A | * | 12/1997 |
| JP | 10-206366 A | * | 8/1998 |
| JP | 2001-108652 A | * | 4/2001 |
| JP | 2001-153836 A | * | 6/2001 |
| WO | WO 97/42497 A1 | * | 11/1997 |
| WO | WO 9946587 A1 | * | 9/1999 |

OTHER PUBLICATIONS

JPO computer English language translation of Tsuneji et al. (JP 2001-108652 A).*

Derwent absrtact of ZH Shio Jigyo Cent[Shio] (JP 10-206366 A).*

Brown, "*Solid-State Liquid Chemical Sensors*", Invited Paper, Chemistry Forum '98: The Fourth International Symposum, Warsaw, Poland, pp. 120-126, (Apr. 27-29, 1998).

Pace et al., "Thick-Film Multilayer Ion Sensors for Biomedical Applications," *Biosensors and Chemical Sensors*, ch. 21, pp. 261-273, (1992).

Atkinson, "*Hybrid Chemical and Physical Sensor Arrays*," Proceedings of the 9th European Hybrid Microelectronics Conference pp. 277-288 (1993).

Siemens Environmental Systems Ltd brochure: "*Censar: A New Concept in Liquid Measurement*" (1999).

Dascore Inc. press release: "*Dascore has now developed a Six CENSE with the ability to measure Chloramines!*" (Apr. 2002).

Siemens Environmental Systems press release: "*Siemens Environmental Systems and Remote Management Systems Join to Protect United States Recreational Waters and Cooling Towers*" (Apr. 2002).

"*Water Testing Lab on a Chip,*" Innovation News (2001).

Wilson et al., "*Chemical Sensors for Portable, Handheld Field Instruments*," IEEE Sensors Journal, vol. 1, No. 4 (2001).

Johnson et al., "*Chlorine Residual Measurement Cell: The HOCl Membrane Electrode*," Journal AWWA (1978).

Mallinckrodt Sensor Systems brochure: "*Gem Systems: Technical Summary*" (1990).

Meyerhoff, "*New In Vitro Analytical Approaches for Clinical Chemistry Measurements in Critical Care*," Clinical Chemistry, vol. 36, No. 8(B) (1990).

Strike et al., "*Spatially Controlled Membrane Depositions for Silicon-Based Sensors*," Chimia 47 pp. 241-244 (1993).

Lauks et al., *Multispecies Integrated Electrochemical Sensor with On-Chip CMOS Circuitry*, IEEE pp. 122-124 (1985).

Siemens Environmental Systems press release: *Censar for Swimming Pools* (Apr. 2002).

Printout of web page from site "http://shop.hach-lange.com/shop/action_q/highlights/highlight_id/l94/lkz/ll/spkz/en/TOKEN/AqzNVcjw_kvZmpxKxJxkf97vy1E/M/CdMmKA" from Hach Lange Company, printed Nov. 22, 2005 (two pages).

* cited by examiner

METHOD AND APPARATUS FOR QUANTITATIVE ANALYSIS

CROSS-REFERENCE TO RELATED APPLICATION

The benefit under 35 U.S.C. §119(e) of U.S. Provisional Patent Application Ser. No. 60/408,806 filed Sep. 6, 2002, is hereby claimed.

BACKGROUND

1. Field of the Disclosure

The disclosure relates generally to a sensory apparatus. More particularly, the disclosure relates to an integrated assembly of sensor elements and a method of determining properties of an analyte, such as the disinfection quality of water, using a sensory apparatus.

2. Brief Description of Related Technology

Water disinfection is predominantly performed via chlorination. Chlorine, unfortunately, also undergoes time-dependent, irreversible degradation into non-active forms (i.e., forms incapable of disinfecting water). Monitoring of actual free chlorine levels in water has therefore become very important in maintaining safe drinking water.

For human health and safety reasons, drinking water must be closely monitored for chlorine content. The optimum chlorine disinfection level has a narrow operating window: too little chlorination presents the risk of microbial growth, and over-chlorination leads to the formation of chlorinated byproducts that are mutagenic.

Extensive water distribution systems complicate matters further, whereby the free chlorine content will vary depending on where water is sampled within the distribution lines.

Prior practice directed to chlorine monitoring has involved independent chlorine-related chemistry measurements without regard to time constraints brought about by chlorine sample instability. Typically, grab samples are obtained anywhere in the distribution system and sent to a laboratory for analysis. The measurements are not meaningful because by the time analytical results are reported they are not reflective of the true chemical state of the sample (e.g., because $Cl_2$ is unstable).

Furthermore, traditional chemical analysis, including analysis for water chemistry, has required the use of a battery of chemical reagents, equipment, and manual manipulation of samples, intermediates, and products, which results in drawbacks such as the time required for analysis, the inability to perform analysis without human intervention, the requirement to stock such reagents and equipment (and for transportation if on-site analysis is desired), environmental hazards associated with disposal of reagents and products, and, not insignificantly, costs.

SUMMARY

One aspect of the disclosure provides an apparatus including a substrate including a plurality of sensors to obtain an analyte profile, the sensors including an ion-selective sensor capable of measuring ion content and a chlorine sensor capable of measuring chlorine content.

Another aspect of the disclosure is a method of generating an analyte profile, including measuring a plurality of ion concentrations, concurrently on a contiguous sample and, preferably, correcting a first concentration or set of concentrations based on a second, independent concentration or set of concentrations.

Further aspects and advantages may become apparent to those skilled in the art from a review of the following detailed description, taken in conjunction with the drawings. While the sensory apparatus and associated methods are susceptible of embodiments in various forms, the description hereafter includes specific embodiments with the understanding that the disclosure is illustrative, and is not intended to limit the invention to the specific embodiments described herein.

DETAILED DESCRIPTION

Figure 1:
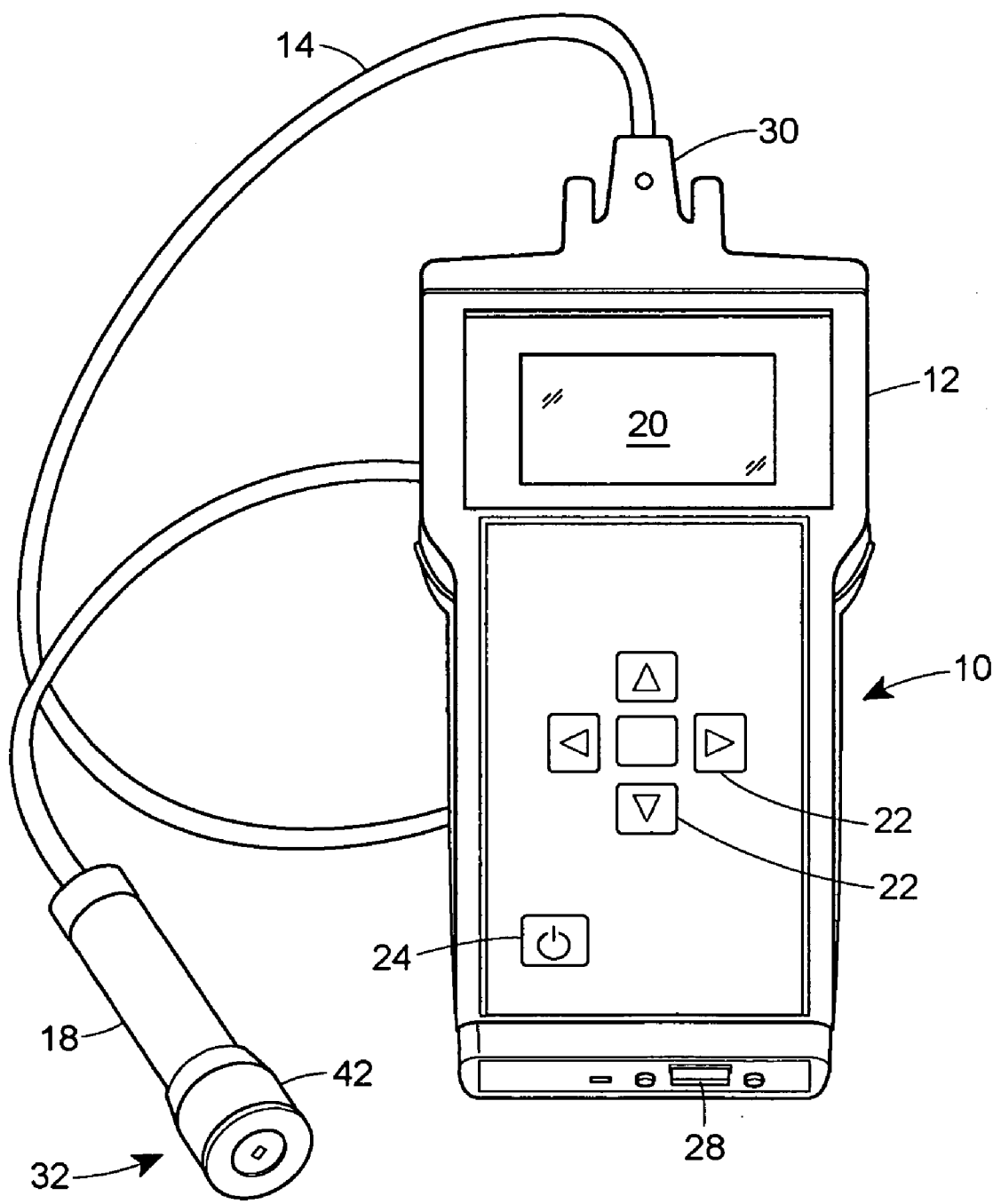
FIG. 1 shows an embodiment of an apparatus according to the disclosure that includes a hand-held analyzer unit connected by a cable to a sensor probe unit.

Free chlorine in water is defined as the concentration of residual chlorine in water present as one or more of dissolved gas ($Cl_2$), hypochlorous acid (HOCl), and hypochlorite ion ($OCl^-$). The three forms of free chlorine typically exist together in equilibrium, and their relative proportions are influenced by the pH and temperature of the water. Total chlorine includes free chlorine and combined chlorine species, such as those available for disinfection (e.g., oxidants such as chloramines). Thus, one measure of a disinfection index is the total concentration of free chlorine. Another measure of a disinfection index is the total concentration of free chlorine and combined chlorine species available for disinfection.

Some of the primary chemical reactions at equilibrium in a typical potable water source are set forth below.

$$Cl_2 + H_2O \leftrightarrow HOCl + H^+ + Cl^- \text{ (free chlorine)} \quad [1]$$

$$HOCl \leftrightarrow H^+ + \underline{ClO^-} \text{ (hypchlorous acid/hypochlorite ion)} \quad [2]$$

$$CO_2 + H_2O \leftrightarrow H_2CO_3 \text{ (carbonic acid)} \quad [3]$$

$$H_2CO_3 \leftrightarrow H^+ + HCO_3^- \text{ (bicarbonate ion)} \quad [4]$$

$$HCO_3^- \leftrightarrow H^+ + CO_3^{2-} \text{ (carbonate ion)} \quad [5]$$

$$Ca^{2+} + CO_3^{2-} \leftrightarrow CaCO_3 \text{ (hardness)} \quad [6]$$

$$NH_3 + Cl_2 \leftrightarrow NH_2Cl + HCl \text{ (m-chloramines)} \quad [7]$$

$$NH_2Cl + Cl_2 \leftrightarrow NHCl_2 + HCl \text{ (di-chloramines)} \quad [8]$$

The chemical reactions are representative of the following aspects of the water chemistry: the hydrolysis of $Cl_2$ to hypochlorous acid [Eq.1] and subsequent ionization equilibria to hypochlorite ion [Eq.2]; carbon dioxide dissolution in water to form carbonic acid [Eq.3] that in turn dissociates to bicarbonate ion [Eq.4] and carbonate ion [Eq.5]; the precipitation equilibrium reaction of calcium with carbonate ion that alters carbonic acid equilibrium and hence pH [Eq.6]; and the reactions between ammonia and chlorine to form chloramines [Eq.7] and [Eq.8]. Although these reactions are often assumed to be at equilibrium, there is a time component associated with such reactions, for example as the result of mass transport limitations and relatively slow chemical kinetics. Also, all of these chemical constituents cross-react to affect the overall mass balance of all chemical constituents.

At neutral pH, chlorine predominantly hydrolyzes to hypochlorous acid (HOCl). The mole fraction of HOCl to total free chlorine is dependent on pH. Also, the acid dissociates to its ionic forms, hypochlorite ion ($OCl^-$) and free hydrogen ($H^+$). This dissociation is reversible, and pH driven.

The actual (total) HOCl content (including ionic forms) is further mediated by water hardness (e.g., $Ca^{2+}$) and carbon dioxide ($CO_2$) dissolved and dissociated to carbonate ion ($CO_3^{2-}$). $CO_3^{2-}$ precipitates calcium and both chemicals affect the HOCl (free chlorine) content by mediating pH. The pH, water hardness, and dissolved $CO_2$ all contribute to total alkalinity. Hence, to accurately determine free chlorine content, all four chemical parameters (free chlorine, pH, water hardness, and dissolved carbon dioxide (including ionic forms)) are measured, directly or indirectly, at the same time.

To further complicate matters, ammonia can be generated by organisms (impurities in water) which will react with free chlorine to form chloramines, such as monochloramine ($NH_2Cl$), dichloramine ($NHCl_2$) and trichloramine ($NCl_3$). Chloramines are also active oxidants and in some treatment plants are the primary disinfectants used. In addition to ammonia, the chloramine concentration is dependent on calcium, pH, and carbonate chemistry. Accordingly, a refined disinfection index can include contributions of chloramines.

To further complicate the measurement, temperature and salt (electrolyte) content variations can further affect the accurate determination of a disinfection index. Temperature can affect ion-selective electrode (ISE) response rates. The ionic strength of the analyte (conductivity measurement) can also affect the accurate measurement of individual ionic species. Temperature and conductivity can also affect the ionization and solubility of chlorine species. Thus, a determination of disinfection index can be further refined by measuring and accounting for one or more of temperature and conductivity. For example, a salinity (conductivity) measurement can be used to compensate for the change in activity coefficient error and the temperature measurement can be used to correct for kinetic effects on ISE sensor elements.

In view of the foregoing, water disinfection monitoring and control can be accomplished via an apparatus and method for chemical profiling of disinfection species (e.g., free chlorine and optionally chloramines) and the chemistry that mediates it (or a dominant portion thereof) to arrive at a disinfection index. Thus, apparatus and methods for performance and analysis of certain chlorine-related chemistry measurements and calculations for determining the disinfection state of a water sample are described herein below.

In one embodiment, the profiling is performed through a network of monitors throughout a distribution system for real time, accurate reporting of true disinfection chemistry throughout the system. The actual chlorine levels are calculated from multiple concurrently-measured parameters. The measured parameters are provided as inputs to an algorithm that computes an effective disinfection index based on the chemical profile (composition) of the water sample.

In a general sense, the apparatus includes a substrate including a plurality of electrode sensor elements adapted to measure relevant species of an aqueous analyte. The sensor elements include, for example, electrodes and selective membranes, which, together with any support circuitry which may be required to drive a sensor element, make up the complete sensor. For example, the substrate can include a plurality of electrodes covered by ion-selective membranes and an amperometric sensor including a working electrode and a counter electrode. In one application, the substrate including the sensor elements is connected to an analyzer capable of calculating one or more desired properties of the analyte, such as the disinfection index of a water sample. Optionally, the substrate includes additional sensor elements configured to measure additional species (e.g., an ammonia sensor, an oxygen sensor, and mutagenic species, such as via immunosensors or DNA probes) and additional physical properties, such as temperature, conductivity, and oxidation-reduction potential.

The apparatus is useful for generating a chemical profile of an analyte that includes a set of species of interest, one or more species of which are in a chemical equilibrium influenced by additional characteristics of the analyte. In accordance with one general embodiment, a real-time test device for analyzing an aqueous analyte includes: a set of ISE-based sensor elements to provide a first series of measurements of properties of the analyte; one or more sets of amperometric sensor elements to provide a second set of measurements of properties of the analyte; and a sensor data analyzer to generate in real-time a desired chemical profile of the analyte. The profile can include concentration levels of a desired species, or set of species. The measurements preferably are taken concurrently and on a contiguous sample of the analyte. The first and second sets of measurements can be supplemented by additional measurements of the analyte, such as temperature and conductivity, to correct for various factors such as sensor response rates and activity coefficients. The real-time test device preferably provides a chemical profile in a reagent-free manner, and without the need for otherwise modifying the solution chemistry of the analyte. For instance, the pH of the analyte need not be modified to arrive at the concentration profile of one or more species.

In accordance with a chlorine water chemistry embodiment, a real-time test device for analyzing water includes: a plurality of ISE-based sensor elements to provide a first series of measurements pertinent to chlorine-related analysis of the water; one or more sets of amperometric sensor elements to provide a second set of measurements pertinent to chlorine-related analysis of the water; and a sensor data analyzer to generate in real-time the chlorine-related analysis of the water, referred to herein as a disinfection index. The disinfection index includes concentration levels of free chlorine, and optionally one or more chloramines or related combined-chlorine disinfectant species. The elements are arranged such that the measurements are taken on a contiguous sample. The apparatus is also configured such that the measurements are taken concurrently. The above-identified sensor elements and functions can be supplemented by additional sensor elements to measure other properties of the water, such as temperature and conductivity, to correct for various factors such as ISE response rates and activity coefficients. The real-time chlorine test device preferably provides a disinfection index in a reagent-free manner, and without the need for otherwise modifying the solution chemistry of the water.

The apparatus preferably includes an amperometric sensor designed to measure HOCl (including ionized forms), varieties of which are known in the art. The additional elements are designed to provide data to correct and/or supplement the HOCl measurement to arrive at a more accurate indication of the free chlorine content. This indication can be still further supplemented via sensors adapted to measure chloramines, for example. Combining the sensor elements on a single substrate and providing an apparatus with a connected analyzer capable of calculating properties of the water allows the user to receive a highly accurate indication of the disinfection state of the water sample.

The real-time test device can utilize micro-array sensor chip technology based on a silicon platform. For example, the above-described ISE-based sensor elements can be implemented in a silicon-based embodiment, such as that as described by Brown, "Solid-state Liquid Chemical Sensors" (Miniaturized Analytical Devices Microsymposium, Chemistry Forum, 1998, pp. 120–126), the disclosure of which is hereby incorporated herein by reference. Alternative silicon-based sensor devices, and the manners in which such devices can be fabricated, are described in U.S. Pat. No. 4,743,954 ("Integrated Circuit for a Chemical-Selective Sensor with Voltage Output"), U.S. Pat. No. 5,102,526 ("Solid State Ion Sensor with Silicone Membrane"), and U.S. patent application Ser. No. 09/768,950 ("Micromachined Device for Receiving and Retaining at least one Liquid Droplet, Method of Making the Device and Method of Using the Device"), the disclosures of which are hereby incorporated herein by reference. The chip platform can be based on other electrochemical solid state sensor technology that is well known in the art, as shown by Brown et al. in Sensors and Actuators B, vol. 64, June 2000, pp. 8–14, the disclosure of which is hereby incorporated herein by reference.

The silicon chip incorporates a combination of chemically-selective sensors and physical measurements that work in concert to deliver chemical profiling information on a test sample as small as one drop. The apparatus offers a total analytical solution on a single chip/package that can be disposable. This technology is ideally suited for water quality and medical diagnostic applications. It further aims to empower the field user with the analytical capacity of a laboratory by providing an easy to use, fast, cost effective, minimum- or no-maintenance, optionally disposable test panel for specific applications. The disposability of such a device can overcome many of the practical problems associated with long-term exposure or, in the case of medical applications, prior sample memory or contamination. Timely, actionable information is the driver for most analytical testing and this lab-on-a-chip approach can be used for real-time, on-line monitoring or point-source analysis with instant results.

Thus, in one embodiment, the apparatus includes a chip-based analytical sensing device designed to permit concurrent, contiguous, and continuous disinfection quality testing. The chip includes a silicon wafer upon which a plurality of sensor elements is formed, the sensor elements including a plurality of electrodes covered by ion-selective membranes and one or more sets of amperometric sensors including a working electrode and a counter electrode. The sensors preferably include a free chlorine sensor (e.g., HOCl and OCl$^-$), a pH sensor, a calcium ion sensor, a carbonate ion sensor, and a bicarbonate ion sensor (e.g., a $pCO_2$ sensor based on pH detection).

Optionally, the substrate can include one or more of a temperature sensor, a conductivity sensor, an ammonia sensor, an oxygen sensor, and an oxidation/reduction potential sensor, preferably on the same chip. The temperature and conductivity sensors can be used to compensate for electrolyte and temperature effects on ISEs. The ammonia measurement can be used for measuring the mass balance regarding chloramines and free chlorine, or as an indicator of microbial contamination. The oxygen measurement can be used to detect the presence of oxygen-consuming chemical or biological activity. The oxygen measurement can also be used to account for reaction of oxygen with chlorine to form chlorine dioxide (alternatively, a chlorine dioxide sensor can be used). The oxidation/reduction potential can be used to detect gross effects due to the microbial load (e.g., for verification that the water is disinfected, despite a marginal or low disinfection index). Immunosensors and DNA probes (e.g., hybridization arrays with oligonucleotides) can also be applied for mutagen and/or pathogen detection given the appropriate coatings on the electrode surfaces.

The analyzer can be a general purpose microprocessor operated by software or firmware, a specialized microprocessor, or a hard-wired algorithm. In a microprocessor embodiment, the algorithm can be hard coded or soft coded (e.g., firmware). The analyzer can be, in whole or in part, a personal computer, a PDA, or a custom unit (such as the hand-held unit described below in connection with the figures).

In one embodiment, the apparatus further includes a power circuit and an analog amplifier circuit in electrical connection with one or more sensor elements and an analog-to-digital converter circuit connected to the amplifier and to a microprocessor, the apparatus configured to amplify a signal produced by a sensor and convert the analog signal to a digital signal for processing. The apparatus can also include additional circuits and/or components for data buffering and storage (e.g., volatile and non-volatile memory), display (e.g., an LCD), and communication (e.g., an RS-232 port).

In a particular embodiment, the free chlorine sensor includes an amperometric sensor including a reference electrode disposed on or off of the substrate; the pH, calcium ion, and carbonate ion sensors each include an ion selective electrode; and the bicarbonate ion sensor is a differential $pCO_2$ sensor including an unbuffered pH-sensitive electrode sensor and a buffered pH-selective electrode sensor, the buffered pH-selective electrode sensor of the differential $pCO_2$ sensor being the same or different as the ion selective electrode of the pH sensor, although any suitable bicarbonate ion sensor or total dissolved $CO_2$ sensor can be used. The substrate can further include an external periphery, including a plurality of bond pads on the periphery electrically connected to circuitry inside the periphery.

Table 1 below provides additional information regarding measured parameters, preferred types of sensors capable of carrying out the measurements, and the manner in which the sensor is operated to obtain the measurement. Some of the measurements preferably are obtained via ion-selective electrode (ISE)-based sensors, the ionophores and other aspects of which are well known in the art. See, for example, Bakker et al. "Carrier-based Ion-selective Electrodes and Bulk Optodes" (Chem. Rev. 1997, Vol 97, No. 8, pp 3083–3132), the disclosure of which is hereby incorporated herein by reference.

TABLE 1

| MEASURED PARAMETER | SENSOR TYPE | SENSOR OPERATION |
|---|---|---|
| Temperature | RTD (resistive temp) | Admittance using 1 kHz/1 V p-p |
| Conductivity | Pair of Au electrodes | AC Impedance |
| Oxidation-Reduction Potential | Pt electrode | Potentiometric |
| pH | ISE | $H^+$ selective membrane |
| $Ca^{2+}$ | ISE | $Ca^{2+}$ selective membrane |
| $CO_3^{2-}$ (total $CO_2$/total alkalinity) | ISE | $HCO_3^-$, $CO_3^{2-}$ surrogates |
| $Cl_2$/HOCl | Amperometric | Electro-reduct./oxidation of $OCl^-$ |
| $NH_2Cl$/$NHCl_2$ | Amperometric | Electro-reduct./oxidation of $NH_2Cl$, $NHCl_2$ |
| $ClO_2$ | Amperometric | Electro-reduct./oxidation of $ClO_2$ |
| $NH_3$ | ISE | Gas membrane with pH sensor |

One or more of the electro-reduction/oxidation operations can be accomplished via AC voltage pulse techniques, and the working electrode associated with any one or more amperometric measurements can constitute an array (e.g., an interdigitated array) of micro-electrodes (e.g., platinum), the currents for which are summed across the array. Such an array using gold electrodes can also be used to measure dissolved chlorine, because the gold acts as a catalyst to activate the surface of the electrode. In one embodiment, each micro-electrode has a 10 micron diameter, with a 100 micron center-to-center distance between adjacent micro-electrodes in the array. Free carbon and oxygen can be measured by such an amperometric micro array.

One HOCl electrode suitable for use with the described method and apparatus is set forth by Johnson et al., "Chlorine Residual Measurement Cell: The HOCl Membrane Electrode" (J. Amer. Water Works Association, June 1978, pp. 341–348), the disclosure of which is hereby incorporated herein by reference.

The ISE membranes can consist of a polyurethane dielectric polymer doped with selective binding agents (ionophores) for ions as the target molecules. The ionophore binds the target ion and selectively extracts the ion into the organic phase. This phase transition of an ion from aqueous sample phase to organic membrane phase results in a very specific (voltage) signal at the membrane surface. The potential measurement for each ISE membrane is compared to a reference electrode, which can be shared among all four ISE sensors. The reference electrode can be on-chip or, preferably, off-chip.

Table 2 below identifies examples of selective ligands for various ISEs, exchangers for additional parameter tests, and ranges of measurement.

TABLE 2

| Parameter | Test | Selective Ligand/ Exchanger | Range of measurement (Molar units) |
|---|---|---|---|
| Potassium | $K^+$ | PU-Valinomycin | $10^{-5}$ to $10^{-1}$ |
| Sodium | $Na^+$ | PU-Calixarene | $10^{-4}$ to $10^{-1}$ |
| Hydronium | pH | Tri-n-dodecylamine | 5 to 9 |
| Calcium | $Ca^{2+}$ | PU-ETH 1001 | $10^{-5}$ to $10^{-2}$ |
| Chloride | $Cl^-$ | Quaternary Ammonium Poly | $10^{-4}$ to $10^{-1}$ |
| Alkalinity | $HCO_3^-$ | Differential Membrane pH | $3 \times 10^{-3}$ to $10^{-1}$ |
| Oxygen | $pO_2$ | Silicon/NAFION membrane | 0 to 300 mmHg |
| Ammonia | $NH_3$ | Silicon-diff. pH or Ammonium ion | $10^{-5}$ to $10^{-1}$ |
| Chlorine | $Cl_2$ | Cellulose-HOCl reduction | 1–10 ppm |
| Oxidation-Reduction | ORP | Potential | 0–1000 mV |
| Temperature | | RTD | 5 to 50° C. |
| Conductivity | salinity | Ti/Pt | 0 to 2000 μS/cm |

To obtain meaningful measurements of the free chlorine level and, more generally, the disinfection state of a water sample, an apparatus and method for performance and analysis of certain chlorine-related chemistry measurements and calculations are described herein below. Preferably, such performance of the method is concurrent in time, contiguous in sample, and continuous in time.

Concurrent means that a set of relevant steps (e.g. measurement, correction of a measurement, or analysis) are performed at substantially the same time. Due to the rapid speed of data analysis using electrical processors, a sequence can be implemented for analysis and the method will still be considered to be performed at substantially the same time. Concurrent measurement allows for correction and accounting for the chemical kinetics driving the overall disinfection state and chemistry of the water sample. While the steady-state measurements performed can correct for and account for chemical equilibrium conditions, some of the solution chemistry may never reach such equilibrium.

Contiguous in sample means that the relevant steps are performed on (or with respect to) substantially the same sample. Sameness of a particular sample will depend on the degree of spatial heterogeneity of the substance sampled, and can also be related to the time-dependent heterogeneity of the substance sampled.

Continuous in time means that one or more relevant steps are each repeated in series during a selected period of time. The method can also be performed by two or more sets of sensor arrays operating in parallel.

For example, a water chemistry determination can be calculated as relevant measurements are performed. Thus, the shipment of samples to a laboratory for testing at a later point in time is not required. The determination also can be continuously updated, for example in an always-on state, or while a button is held depressed. Furthermore, the time-dependent changes in the composition of a sample can be negated (as in the case of a concurrent measurement) or tracked (as in the case of continuous operation).

According to the disclosed method, chlorine is measured as hypochlorous acid reduction and its mole ratio to hypochlorite ion is pH dependent according to the equilibrium chemistry described. The method includes independent measurements (direct or indirect) for $Ca^{2+}$, pH, bicarbonate, and carbonate, which are in turn provided as inputs to an algorithm that calculates corrected free chlorine concentration. A salinity (conductivity) measurement can be used to compensate for the change in activity coefficient error and the temperature measurement can be used to correct for effects on ISE response rates. The conductivity measurement can also be used to make minor corrections for liquid junction potentials that can be significant with the salinity variations of surface waters. To be useful, such measurement corrections can only be performed concurrently on a contiguous sample, a feature that is inherent in the IC arrays described herein but lacking in known systems.

The chemistry for chloramines follows similar interdependencies relative to ammonia, pH, ionic and gas content. Free chlorine will react with ammonia to form mono- and di-chloramines. The mass balance between chloramines, ammonia, and chlorine is dependent on pH, ionization equilibrium (ammonium hydroxide formation) and cross-reactivity with other gasses, such as oxygen and carbon dioxide.

Generally, a method of generating a disinfection index of water, includes measuring, directly or indirectly, properties of a water including free chlorine concentration, pH, calcium ion concentration, carbonate ion concentration, and bicarbonate ion concentration, concurrently on a contiguous sample of water. One or more of the free chlorine species are then adjusted based on measured pH, calcium ion, and total $CO_2$ values and then weighted, for example by an empirical factor. The disinfection index is then calculated as the sum of the adjusted concentrations, for example as represented in [Eq.9] below.

$$I_d = w_1 \cdot x(HClO) \cdot [a_{pH} \cdot b_{Ca} \cdot c_{TotCO_2}]$$
$$+ w_2 \cdot x(ClO^-) \cdot [a_{pH} \cdot b_{Ca} \cdot c_{TotCO_2}]$$
$$+ w_3 \cdot x(Cl_2) \cdot [a_{pH} \cdot b_{Ca} \cdot c_{TotCO_2}] \quad [9]$$

wherein $I_d$ is the disinfection index, $w_1$, $w_2$, and $W_3$ are empirically-derived weighting factors, x is the mole fraction of chlorine species (e.g., HClO and ClO⁻ are measured, and $Cl_2$ is calculated based on pH), and $a_{pH}$, $b_{Ca}$, and $c_{TotCO_2}$ are empirically-derived adjustment coefficients based on pH, calcium ion concentration, and total $CO_2$ concentration (e.g., calculated via direct or indirect carbonate and bicarbonate ion measurements), respectively.

In an improved method, one or more of the measured values is corrected (if necessary) based on temperature and/or conductivity measurements, preferably both and in the order recited.

The empirically-derived correction factors can be determined by known methods for calibrating such sensors as a function of temperature and conductivity. For example, an ISE can be calibrated using a matrix of test solutions having varying known concentrations of the ion of interest and total ionic strength at a constant temperature to yield a correction factor for the ISE depending on measured concentration of the ion of interest and measured conductivity.

Empirically-derived coefficients and weighting factors can be determined by fitting output data from an overall test algorithm, or portions thereof, to known test solutions. Thus, for example, empirically-derived factors can be determined by systematically varying the concentrations of measured parameters in real water samples (e.g., drinking water, potable water, surface waters) which include real water matrices with all matrix constituents. The coefficients and weighting factors can be derived from the effect of the controlled variable (e.g., $Ca^{2+}$ hardness). Such factors can be refined by the accumulation of substantial (statistically significant) data sets over a variety of water matrices.

Coefficients and weighting factors can also be derived by accounting for species in equilibrium based on the equilibrium constant and reaction rate at the measured conditions. The number and complexity of interrelated reactions, even in potable water, can yield inaccurate results using only such derived parameters, although such calculations can be useful as a starting point for determining empirically-derived weighting factors. The empirical approach circumvents the need to define such a disinfection index by theoretically accounting for all the reactions that affect chlorine.

The correction factors, adjustment coefficients, and weighting factors can be made available for use by storage in the form of a lookup table, for example in a memory connected to the analyzer, or can be coded in the form of an algorithm (e.g., correction factor to the conductivity sensor as a function of temperature).

The method can optionally include calculating free chlorine species concentrations as a function of pH, weighting one or more of the calcium ion, carbonate ion, bicarbonate ion, and free chlorine species concentrations by an empirical factor; and then calculating a disinfection index as the sum of the products of each of the free chlorine species with the remainder of the concentrations.

The method can include repeating the method in series or parallel and reporting a disinfection index as the average of two or more discrete disinfection indices. The method can also include measuring temperature and applying a kinetic coefficient correction to one or more of the measured properties, and measuring conductivity and applying an activity coefficient correction to one or more of the measured properties.

In a preferred method, the temperature measurement is first used to correct one or more sensor values (e.g., ISEs, conductivity, and free chlorine amperometric sensors), the conductivity measurement is then used to assign activity coefficients for ISEs, and then the corrected ISE and free chlorine measurements are used to derive a disinfection index. Although the steps have been recited in a preferred order, their operation can be, and preferably is, preformed practically simultaneously in the analyzer.

In accordance with one embodiment, a method of using a water testing panel monitors the disinfection chemistry of drinking water, and can be used in connection with chlorination apparatus to control the disinfection index. Free chlorine in water is primarily affected by pH, water hardness ($Ca^{2+}$) and dissolved $CO_2$, and secondarily by one or more of temperature and salinity. All these factors function in concert to mediate active disinfectant chlorine species content in water. Hence, to closely control chlorine and prevent under or over chlorination, the relevant chemistry preferably is monitored concurrently. A combination of measurements can be performed concurrently on a contiguous sample, and continuously in real-time. The calculated disinfection index and one or more additional measured or calculated parameters can be used as inputs to closely control chlorine within a narrow operating window. More importantly, monitoring the disinfection state in the water distribution systems after it leaves a treatment plant is becoming increasingly important to the protection of public health.

Figure 2:
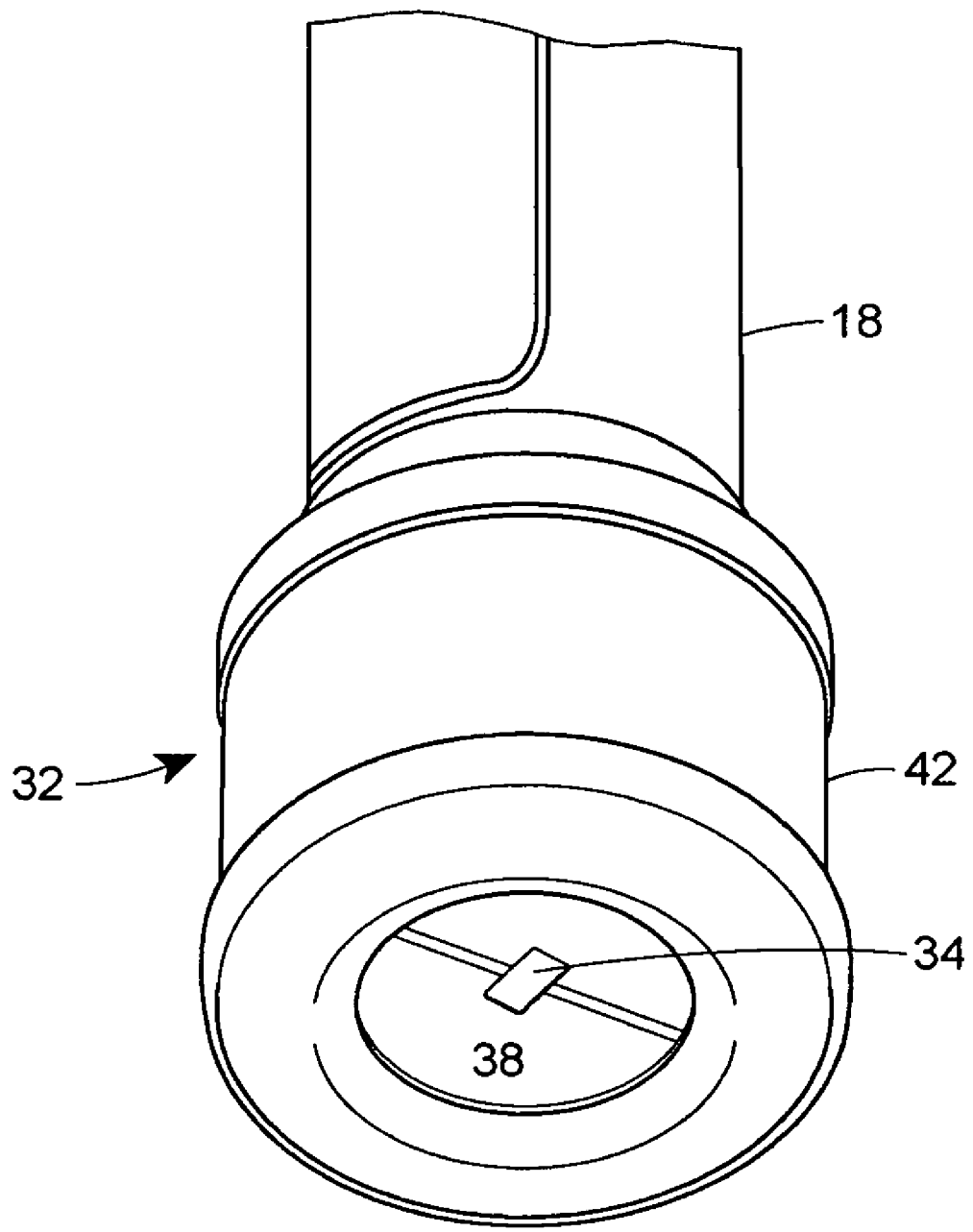
FIG. 2 is an enlarged view of the sensor probe unit of FIG. 1.

FIG. 1 shows an embodiment of an apparatus 10 according to the disclosure that includes a hand-held analyzer unit 12 connected by a cable 14 to a sensor probe unit 18 (also shown in enlarged view in FIG. 2). The hand held analyzer unit 12 includes an LCD 20 for displaying desired information, such as control menus and analysis results. As shown, the hand-held unit 12 also includes control buttons 22 (e.g., scroll keys) and a power button (key) 24. The bottom of the hand-held unit 12 also includes an RS-232 port 28 for connection with additional external apparatus, such as a data storage unit, a PC, and the like. The cable 14 also includes a connector 30 that plugs into a counterpart connector (not shown) on the top of the hand-held unit 12.

The sensor probe 18 (see FIGS. 1 and 2) includes a probe tip 32 having an exposed face of the sensor chip 34 mounted in flip-chip configuration on a lead frame 38.

Figure 3:
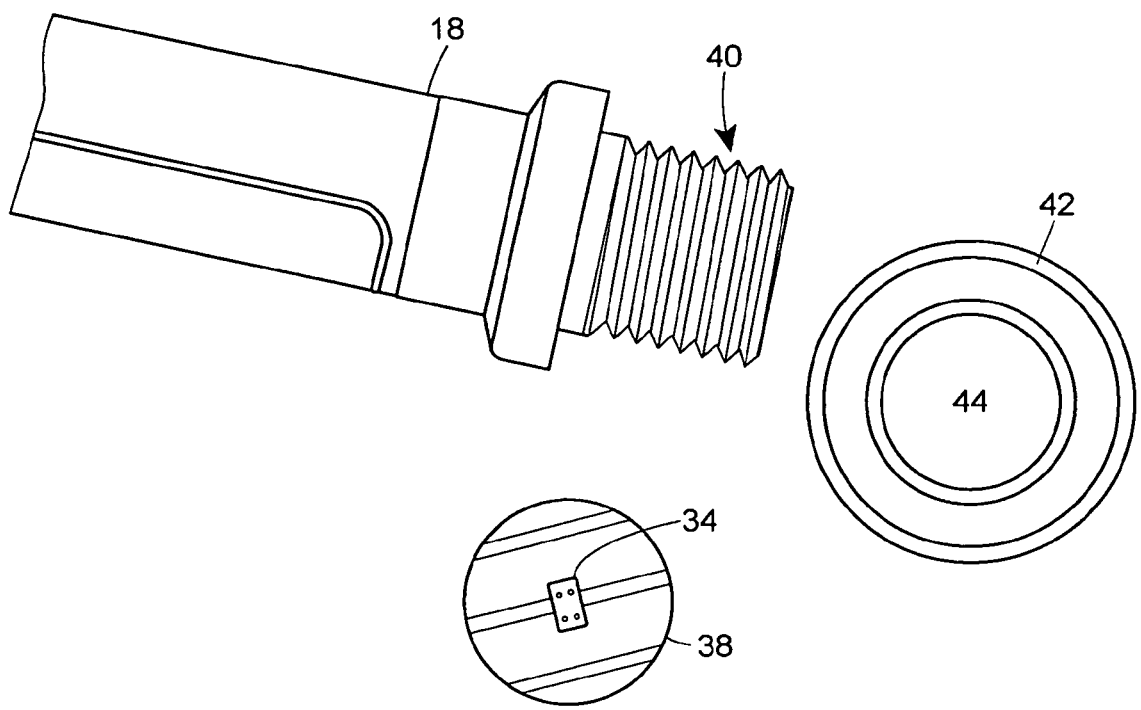
FIG. 3 shows the sensor probe in unassembled form, with the lead-frame and mounted chip assembly separated from the housing (shown in side profile view) of the probe.

FIG. 3 shows the sensor probe 18 in unassembled form, with the lead-frame and mounted chip assembly (34 and 38) separated from the housing (shown in side profile view) of the probe 18. As shown, the housing has a threaded end 40 for connection with a complementary-threaded cap 42 (shown in plan view above the end face of the cap). The cap 42 threads onto the end 40 of the housing of the probe 18 to compress an o-ring type seal (not shown) between the cap 42 and the lead frame 38 to form a water-tight seal and protect the backside electronics of the sensor chip 34 and lead frame 38. The sensor chip 34 and lead frame 38 are exposed to an analyte through the hole 44 in the cap 42.

Figure 4:
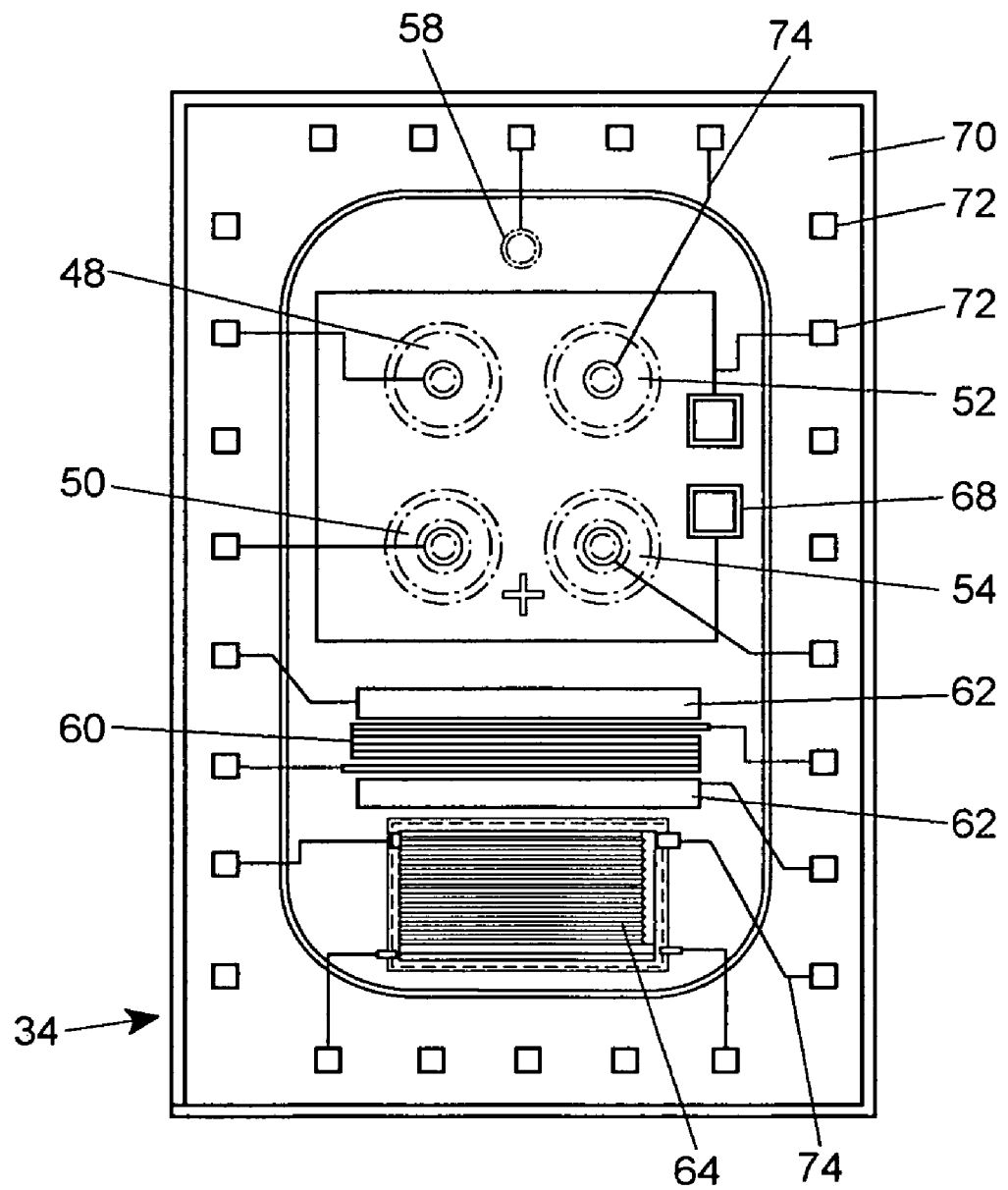
FIG. 4 shows a sensor chip layout according to one embodiment of the device.

FIG. 4 shows the sensor chip 34 layout according to one embodiment of the device. The sensor chip includes ISE sensor elements for calcium ion 48, hydrogen ion (pH) 50, bicarbonate ion 52, and carbonate ion 54, an oxidation-reduction potential (ORP) sensor element 58, a temperature sensor (RTD) 60, a conductivity sensor 62, a chlorine sensor array 64, and an on-chip reference electrode 68, each formed on the chip. Each of the sensor elements can be formed on a silicon substrate via known methods. The chip also includes an external periphery 70, including a plurality of bond pads 72 on the periphery 70 electrically connected to circuitry inside the periphery (e.g., via lead lines 74).

In one embodiment, the silicon platform chip can be an IC with dimensions of 3.4 mm by 4.7 mm with a combination of six selective membrane ISEs and three amperometric sensors. Also within the die are conductivity and temperature (RTD) sensors. The ISEs can be designed to measure ions such as $Ca^{2+}$, $K^+$, $Na^+$, $Cl^-$ and $HCO3^-$ while the amperometric sensors can be designed to measure trace heavy metals (such as As, Pb, Zn, Fe and Cu) and dissolved gasses such as $O_2$, $NH_3$ and $Cl_2$. The IC electrode sites can be coated in various membrane and coating combinations during manufacture known to those skilled in the art. Based on the foregoing additional parameter measurements and other aspects of the chip, it should be understood that the analytical capacity of the chip can go well beyond the measurements necessary for a disinfection chemistry panel.

The array of selective chemical sensor responses can be used to characterize a chemical fingerprint of a unique composition indicative of "unknown" substances. Such substances alter the chemical "fingerprint" much as chlorine is altered by the cross-reactivities of ionic and gaseous constituents. Such fingerprints may constitute both composition and time components as identifiers. Such techniques combined with pattern recognition algorithms can be a useful tool in the detection of chemical and biological hazards.

The membrane dimensions in a preferred embodiment are approximately 300 μm diameter and 10 μm thick which translates to an approximately 3 nL membrane solution volume. Membrane thickness uniformity of +/−0.1 μm imposes a volume metering accuracy of 30 pL. Such uniformity drives sensor performance as it impacts response time constants, drift rates, and off-sets. Spin coating lithography can be utilized to achieve optimal membrane thickness uniformity for arrays of identical sensors.

Preferably, complexity at the chip level is relied upon to integrate the multiple sensors in a single device using membrane patterning. Alternatively, the complexity can be at the packaging level, in which case the sensors are fabricated separately. However, with this trade-off comes tooling and dispensing complexity. The preferred dispense technology for achieving precision volume metering is ink jet printing. Selection of membrane composition and array location can be accomplished in accordance with processes known in the art, including those taught by S. J. Pace and J. D. Hammerslag, ACS Symposium Series, 478, (1992), p-261, "Thick-Film Multi-layer Ion Sensors for Biomedical Applications," the disclosure of which is hereby incorporated herein by reference.

The packaging of the chip in one embodiment includes the integration of electronics (e.g., the analysis unit) and solution sensing, while isolating the two so that neither corrupts the other. A flip chip lead frame assembly that attaches the bond pads to the lead frame is one embodiment. This configuration and assembly procedure maintains the availability of active sensor sites for fluid contact. This configuration and assembly procedure also extends lead termination to the chip and isolates the sensor surface from the electronics. The lead frame can be rigid and, in high value applications, it is adaptable to ASICs and RF communication chip mounts.

In another embodiment, a silicon-based integrated sensor die is attached to a multiconductor circuit substrate by an adhesive, such as a thermoset adhesive. Electrical connections between the substrate and sensor die are made by metallic wire bonds. The electrically conductive elements are completely encapsulated with an insulative material, such as thermoset epoxy, urethane, or silicone. This encapsulation is selective, as it does not encroach on the active sensing portion of the die. Selectivity can be achieved by means of a rectangular dam-shaped feature resident on the sensor die. In this embodiment the circuit substrate is multi layered with connector contacts on the opposite side of the board as the die.

Figure 5:
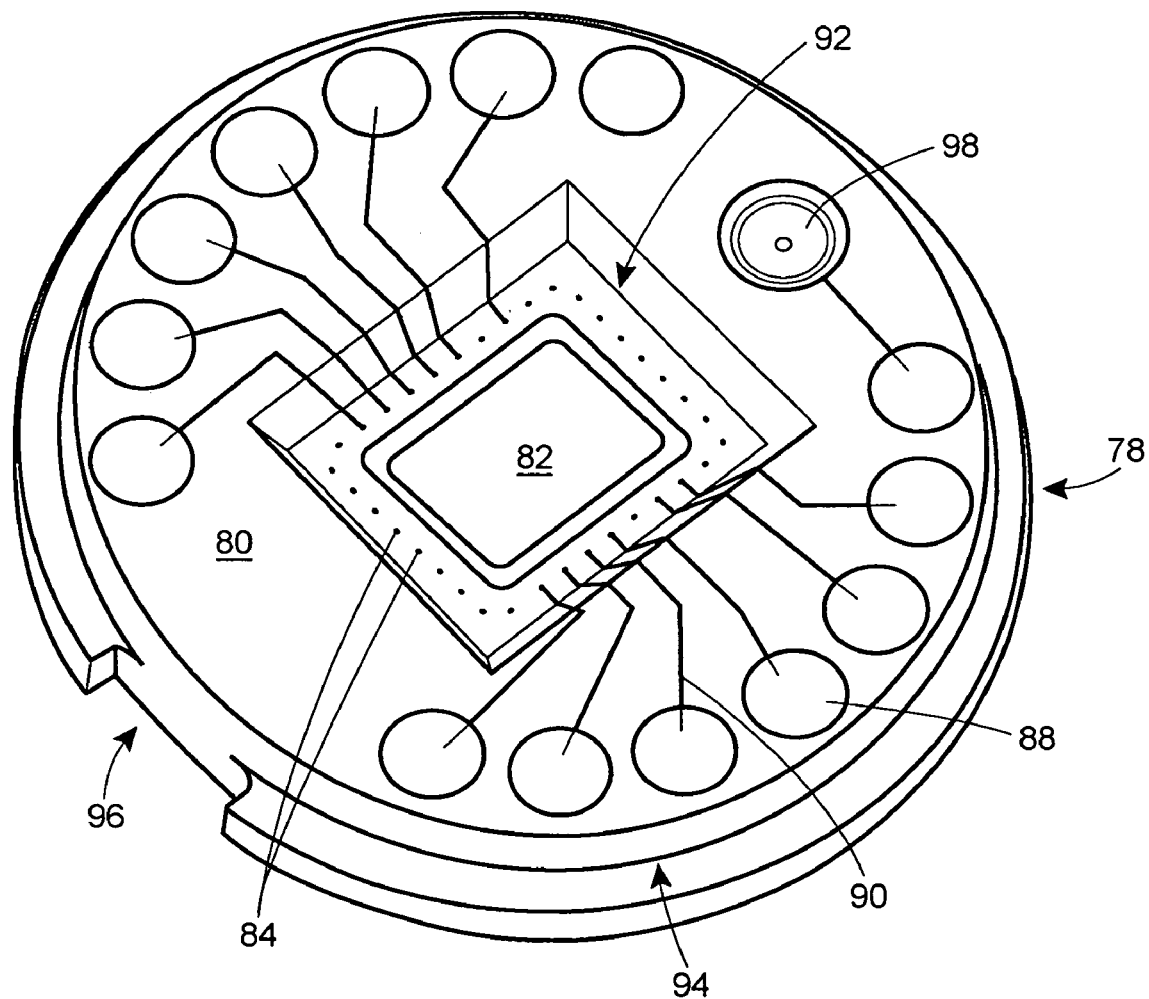
FIG. 5 illustrates an embodiment of a lead frame for flip chip mounting, prior to mounting the sensor chip (not shown).

In one embodiment, such as that shown in FIG. 4, the sensor elements 48 to 68 and at least one bond pad, preferably all bond pads (elements 72 as shown), are all on the same side of said substrate, to facilitate physical and electrical connection to a lead frame in flip-chip fashion (see, e.g., FIG. 5).

FIG. 5 illustrates an embodiment of a lead frame 78 for flip chip mounting, prior to mounting the sensor chip 34 (not shown). The lead frame 78 has a plurality of sides (side 80 shown) and includes an opening 82 through which the sensors (not shown) are exposed for use. The lead frame 78 includes one or more exposed conductor areas 84 (a plurality are shown) aligned for electrical contact with one or more bond pads 72 (see FIG. 4), and a plurality of electrical terminators 88 (a plurality of conductive contact pads for interface with pogo pins are shown), at least one electrical terminator 88 being disposed on the same side of the lead frame 78 as the exposed conductor area 84 and electrically connected to the exposed conductor area 84, e.g., by wire bonds 90. As shown, all electrical terminators 88 are on the same side 80 of the lead frame 78 as the exposed conductor areas 84.

The embodiment shown in FIG. 5 includes a recessed area 92 for accepting the sensor chip 34 (not shown), and a periphery 94 for accepting an o-ring type seal (not shown) in connection with assembling the lead frame 78 in a water-tight package. The periphery 94 also includes a notch 96 for aligning the lead frame when mounted such that the conductive contact pads 88 contact counterpart pogo pins (not shown) when assembled. The embodiment shown also includes an off-chip reference electrode 98 connected by a wire bond 90 to a conductive contact pad electrical terminator 88.

Figure 6:
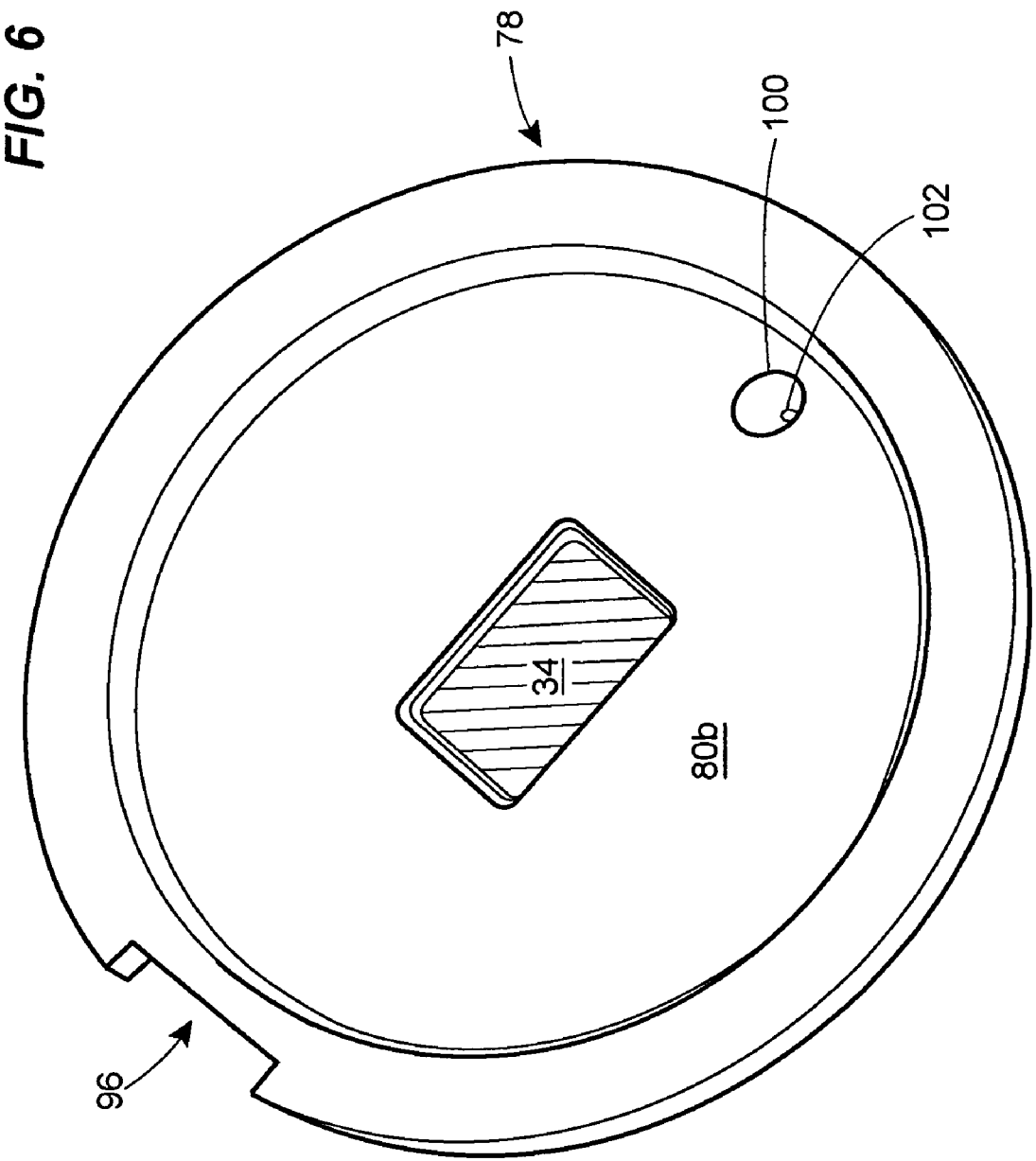
FIG. 6 illustrates the reverse side of the lead frame of FIG. 5, shown with the exposed sensor element face of the sensor chip.

FIG. 6 illustrates the reverse side 80b of the lead frame 78, shown with the exposed sensor element face of the sensor chip 34. This embodiment includes an access hole 100 to permit analyte to contact an exposed face 102 of the reference electrode 98.

Figure 7:
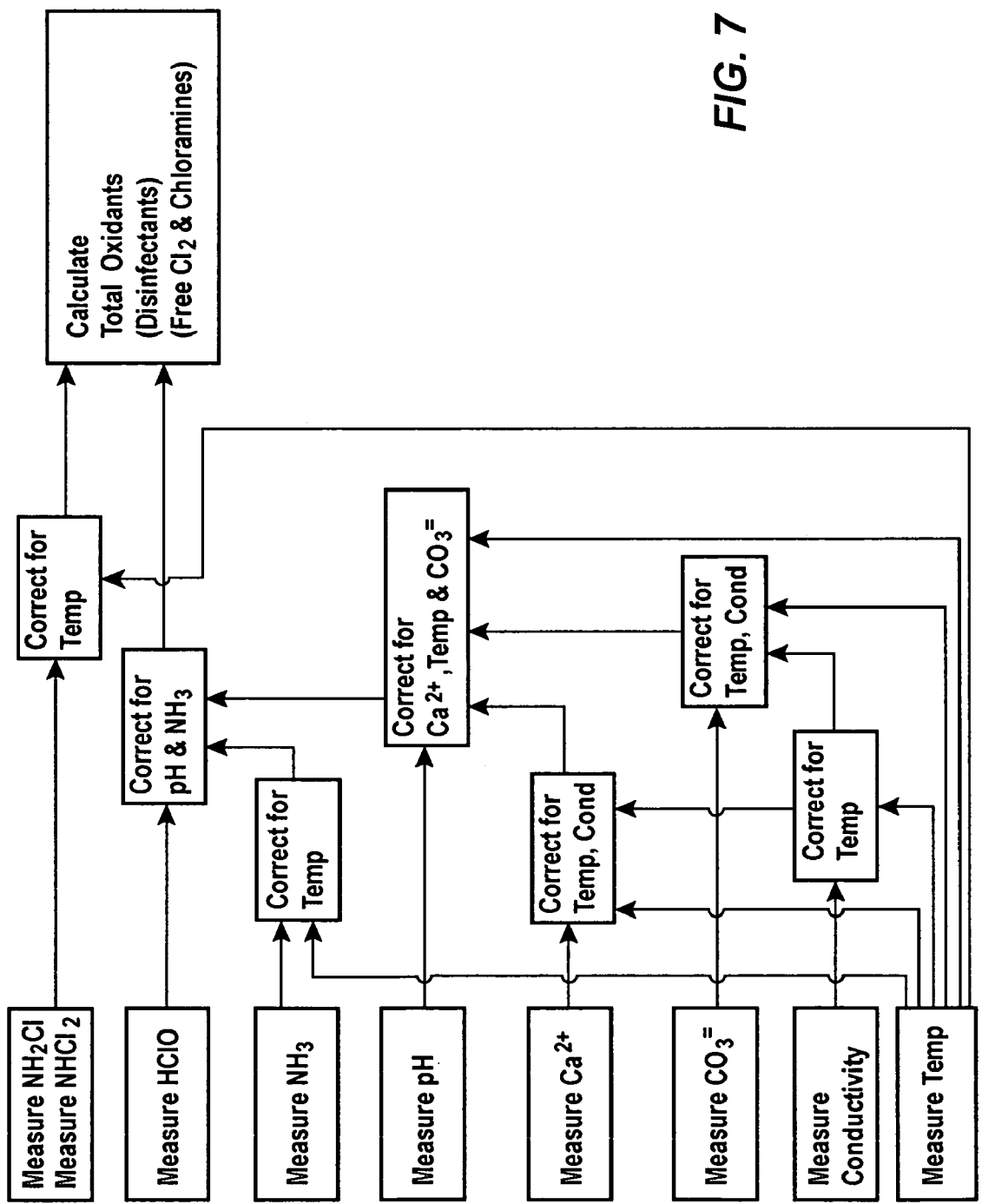
FIG. 7 is a flow diagram summarizing the operation of an embodiment of a sensor apparatus according to the disclosure.

Operation of an embodiment of a sensor apparatus according to the disclosure is summarized in the flow diagram of FIG. 7. For each measurement cycle and, more particularly, for each calculated value of the disinfection state of the water being tested, a number of water chemistry parameters are measured, as shown in FIG. 7. These initial steps include the measurement of correction factors, such as temperature and conductivity, and other equilibrium reactants, such as bicarbonate, $Ca^{2+}$, pH, and ammonia. One or more of the parameter measurements are then corrected (or adjusted) via the values obtained for the correction factors. For example, in the algorithm shown, measurements for chloramines, ammonia, pH, calcium ion concentration, bicarbonate ion concentration, and conductivity are each corrected based on the temperature measurement. Furthermore, both the calcium ion concentration and bicarbonate ion concentration measurements are corrected for conductivity. The pH measurement is adjusted based on calcium ion and bicarbonate ion concentrations. The hypochlorous acid measurement is then adjusted based on the pH and ammonia measurement to yield total free chlorine and combined with the one or more corrected chloramine concentrations to yield a disinfection index based on free chlorine and chloramine oxidants.

The manner in which the adjustments are made can be incorporated into an algorithm in accordance with empirical or other predetermined data obtained via standardized or known water samples. This preferred disinfection index is not limited to free chlorine measurement, but rather incorporates the disinfective activity of both the chloramine and free chlorine corrected concentrations to determine a total disinfection index for the water sample. Other algorithms can be fashioned, taking into account corrections and adjustments of one or more measured parameters in various combinations, based on known equilibria chemistry and empirically-derived coefficients for the analyte of interest.

The disclosed multiple sensor approach profiles chemical information that cannot be achieved by singular tests. In the water disinfection case, dissolved and dissociated carbon dioxide, pH, and water hardness (e.g., calcium) all affect the measurement of the disinfection level of chlorine. Moreover, the information can be delivered in real time and on a contiguous sample. This is a situation where relatively less accurate and precise data actually can provide more significant and actionable information because it more truly represents the sample's makeup and stability (timeliness). For example, the chlorine disinfectant level is unstable in time—if water is collected anywhere in a municipal distribution system for laboratory analysis, by the time the laboratory conducts the test, the chemical composition is no longer representative of the sample. The same holds true for point-of-care diagnostics—information at the bedside is more valuable in life threatening situations than all the controls offered by a state-of-the-art laboratory.

The disclosed multiple sensor approach offers accurate real-time information that extends well beyond the conventional measures of analytical performance. Timely and accurate information helps to solve problems and satisfy application needs. Whether the monitoring issue relates to water safety, life and death medical situations or anti-terrorism, detection speed and all-inclusive indicators and information are critical to effective decision making. Sensor arrays assess cross-reactivities, interactions, interferences and error factors, all through chemical profiles. Such silicon chip arrays represent a viable approach to a total analytical solution for critical testing of water.

EXAMPLES

Example 1

A set of sensors was formed on a silicon substrate to make a sensor apparatus as described herein. The apparatus included pH, $Ca^{2+}$, and $CO_3^{2-}$, and bicarbonate ($pCO_2$) ISEs, having silver/silver chloride electrodes covered by a hydrogel layer (buffered or unbuffered, as described below). The hydrogel layer was covered and sealed by an inner seal membrane, and the inner seal membrane was covered by an ion-selective membrane. An amperometric chlorine sensor array was formed by interdigitated platinum working and counter electrodes, selectively covered by a silicon nitride dielectric material to form an array of exposed electrode portions. A platinum counter-electrode was also formed on the chip. The chip also included a platinum electrode conductivity sensor, and an RTD temperature sensor, and an ORP electrode.

The internal buffer solution used for the pH, $Ca^{2+}$, and $CO_3^{2-}$ electrodes consisted of a mixture of 4 wt. % poly (vinyl)alcohol (PVA) (31,000 to 50,000 molecular weight (MW), 97% hydrolyzed), 0.2M 2-(N-morpholino)ethane-sulfonic acid (MES) (pH 5.5 using LiOH), and 10 mM $CaCl_2$.

The $pCO_2$ electrode internal buffer solution consisted of a mixture of 0.5 wt. % poly(acrylamide-co-acrylic acid) (PAA) (about 15,0000,0000 MW, pH 8.9, 1.5 wt. % acrylic acid), 0.5 mM NaCl, 5 mM NaHCO3, and 1 mg/mL carbonic anhydrase (93% protein (biuret), 5,215 W-A units/mg prot.).

The inner seal membrane and ion selective membranes each included an amount of Outer Membrane Base consisting of a mixture of 9.43 wt. % TECOFLEX polyurethane, 3.14 wt. % poly(vinyl)chloride (PVC) (high molecular weight), 45.1 wt. % cyclohexanone, and 42.3 wt. % tetrahydrofuran.

Each ISE included an inner seal membrane that consisted of 5% HUMISEAL 1A20 polyurethane conformal coating, 11% Outer Membrane Base, and cyclohexanone. The inner seal membrane was disposed on top of the hydrogel, below the ion-selective membrane. The inner seal membrane bonds the ion-selective membrane to the hydrogel and forms a polymer film that provides an excellent seal for the hydrogel.

The pH and $pCO_2$ electrode outer membranes consisted of a mixture of 1.0 g Outer Membrane Base, 140 µL 2-nitrophenyl-octylether, 11.5 mg tridodecylamine, 5.4 mg potassium tetrakis (4-chlorophenyl) borate, 295 µL cyclohexanone, and 295 µL tetrahydrofuran.

The $Ca^{2+}$ outer membrane consisted of a mixture of 1.0 g Outer Membrane Base, 242 µL of 2-nitrophenyl-octylether, 3.8 mg ETH 1001 Calcium Ionophore I, 1.6 mg potassium tetrakis (4-chlorophenyl) borate, 295 µL cyclohexanone, and 295 µL tetrahydrofuran.

The $CO_3^{2-}$ outer membrane consisted of a mixture of 0.5 g Outer Membrane Base, 138 µL bis(2-ethylhexyl) sebacate, 19.2 mg Fluka Carbonate III (FW 399.5) 0.1 mg/µl tetrahydrofuran (THF), 8 mg tridodecyl methyl ammonium chloride), 150 µL cyclohexanone, and 150 µL tetrahydrofuran.

Example 2

Figure 8:
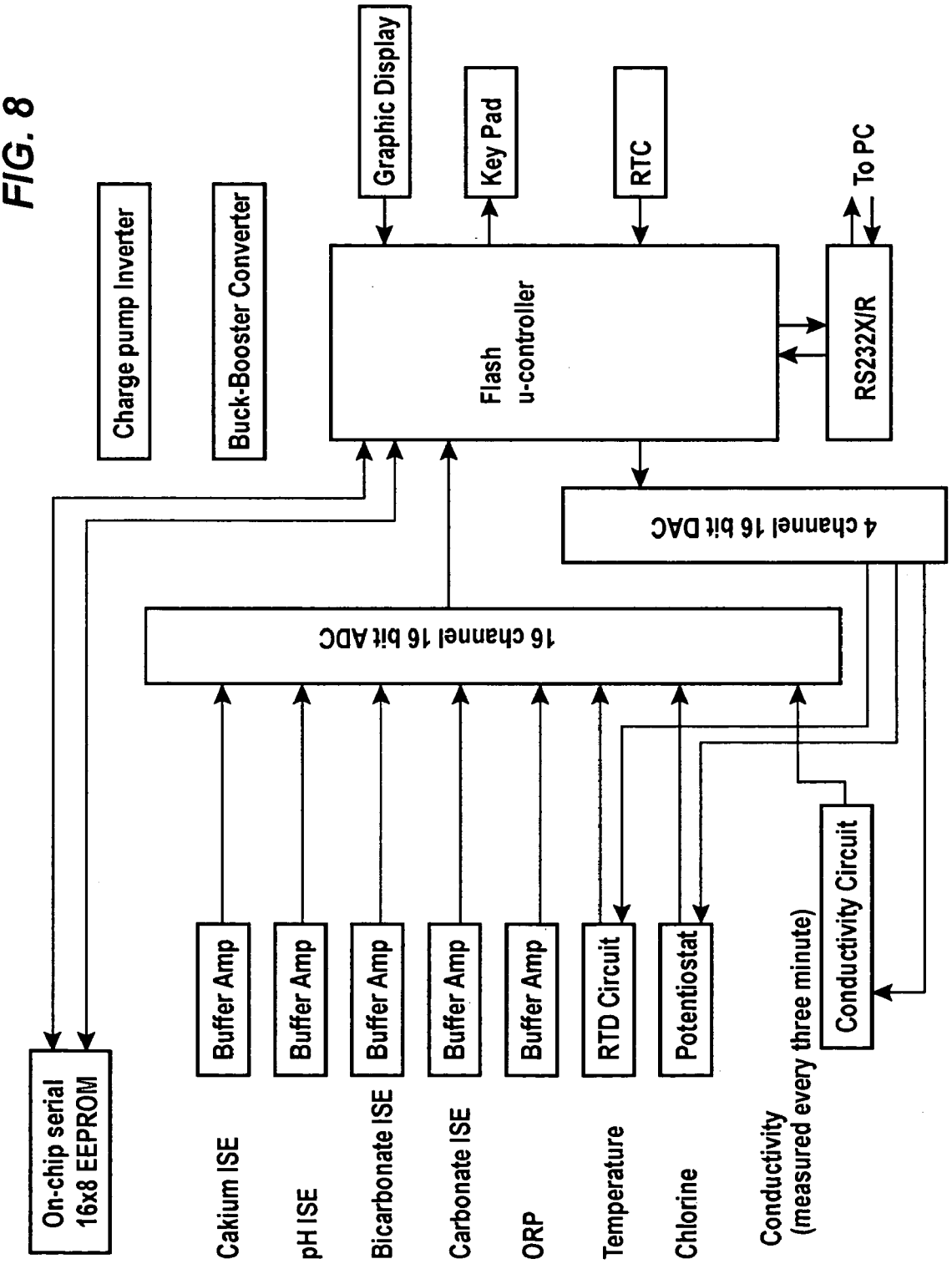
FIG. 8 is a block diagram illustration of the operation of an embodiment according to the disclosure.

FIG. 8 is a block diagram illustration of the operation of an embodiment according to the disclosure.

A bank of buffer amplifiers are configured for voltage measurements (preferably high input impedance voltage measurements) for the identified ISEs and ORP, and for voltage-controlled current measurement for chlorine. The conductivity and RTD measurements are impedance/admittance measurements (e.g., AC) and apply a sinusoid voltage waveform generated by the microprocessor/controller (labeled as "Flash u-controller"), and applied as an analog waveform through the DAC. All outputs of the analog buffer amplifiers are input to the ADC and digital signal input to the microprocessor. The data is reduced to concentration units and reported through the graphic display. All data control and reduction software resides in the microprocessor. A digital communication interface (RS-232) is provided as a PC interface for graphical and supplemental data display. The microprocessor also controls the graphic display via keypad interface and also an EPROM for ID data storage.

A charge pump inverter and a buck booster converter may be included, generally speaking, for power supply purposes in connection with the voltage requirements of various other components in the analyzer unit. The charge pump inverter takes a +5 DC volt input and generates a −5 DC volt output that may be used, for instance, as the other power rail for operational amplifiers. The buck booster converter is a voltage converter that generates other DC Volt levels (e.g., +3 DC volt, +6 DC volt) for other components that do not utilize the standard +5 DC volt supply. The charge pump inverter and the buck booster converter are therefore connected as necessary with the components being powered by the DC voltages to be generated.

What is claimed is:

1. A sensory apparatus comprising:
 a substrate comprising a plurality of sensors to obtain an analyte profile, the sensors including an ion-selective sensor capable of measuring ion content and a chlorine sensor capable of measuring chlorine content, a pH sensor comprising an ion-selective electrode same or different as said ion-selective sensor, and further comprising a bicarbonate ion sensor which is a differential $pCO_2$ sensor comprising an unbuffered pH-sensitive electrode sensor of said differential $pCO_2$ sensor being the same or different as the ion selective electrode comprising said pH sensor.

2. The apparatus of claim 1, further comprising an analyzer that corrects the chlorine sensor measurement based on the analyte profile.

3. The apparatus of claim 2, wherein the substrate further comprises one or both of a temperature sensor and a conductivity sensor.

4. The apparatus of claim 3, wherein said analyzer is configured to analyze a signal from one or both of said temperature sensor and said conductivity sensor to independently correct one or more other sensor measurements.

5. The apparatus of claim 1, wherein said ion-selective sensor is a calcium ion sensor.

6. The apparatus of claim 1, wherein said ion-selective sensor is a carbonate ion sensor.

7. The apparatus of claim 1, wherein said chlorine sensor is configured to measure free chlorine and total chlorine.

8. The apparatus of claim 1, wherein said chlorine sensor is amperometric.

9. The apparatus of claim 1, comprising a plurality of ion-selective sensors, including a hydrogen ion sensor, a calcium ion sensor, and a carbonate ion sensor.

10. The apparatus of claim 1, wherein said substrate further comprises one or more of an ammonia sensor, an oxygen sensor, and an oxidation/reduction potential sensor.

11. The apparatus of claim 1, wherein said substrate comprises a silicon wafer upon which said sensors are formed, said substrate further comprises an external periphery, including a plurality of bond pads on said periphery electrically connected to circuitry inside said periphery.

12. The apparatus of claim 11, wherein said sensors and at least one bond pad are all on the same side of said substrate, and said substrate is physically and electrically connected to a lead frame, said lead frame having a plurality of sides and comprising
 an opening through which said sensors are exposed for use;
 at least one exposed conductor area aligned for electrical contact with said bond pad;
 a plurality of electrical terminators, at least one electrical terminator disposed on the same side of said lead frame as said exposed conductor area and electrically connected to said exposed conductor area.

13. An apparatus for analyzing water quality, comprising: a plurality of ion-selective sensors for measuring ion content of the water, each ion-selective sensor including a sensor element comprising an electrode and an ion-selective membrane on a substrate wherein at least one ion-selective sensor comprises a pH sensor; an amperometric chlorine sensor, the chlorine sensor including a sensor element comprising a working electrode and a counter electrode on said substrate; a bicarbonate ion sensor which is a differential $pCO_2$ sensor comprising an unbuffered pH-sensitive electrode sensor and a buffered pH-selective electrode sensor, said buffered pH-selective electrode sensor of said differential $pCO_2$ sensor being the same or different as the ion selective electrode comprising said pH sensor; and an analyzer unit connected to the sensor elements, wherein the sensor elements transmit signals to the analyzer and wherein the analyzer calculates an analyte profile based on said signals.

14. A sensory apparatus comprising:
 a substrate comprising a plurality of sensors, including
 a free chlorine sensor;
 a pH sensor comprising an ion selective electrode;
 a calcium ion sensor;
 a carbonate ion sensor; and
 a bicarbonate ion sensor which is a differential $pCO_2$ sensor comprising an unbuffered pH-sensitive electrode sensor and a buffered pH-selective electrode sensor, said buffered pH-selective electrode sensor of said differential $pCO_2$ sensor being the same or different as the ion selective electrode comprising said pH sensor.

15. The apparatus of claim 14, wherein said free chlorine sensor comprises an amperometric sensor comprising a reference electrode disposed on or off of the substrate; and said calcium ion and carbonate ion sensors each comprise an ion selective electrode.

16. A sensory apparatus, comprising:
 a substrate comprising a plurality of sensors, including:
 a chlorine sensor;
 a pH sensor comprising an ion selective electrode;
 a conductivity sensor;
 a temperature sensor;
 a first ion selective electrode sensor;

a second ion selective electrode sensor configured to measure a different ion than the first ion selective electrode sensor;

a bicarbonate ion sensor which is a differential $pCO_2$ sensor comprising an unbuffered pH-sensitive electrode sensor and a buffered pH-selective electrode sensor, said buffered pH-selective electrode sensor of said differential $pCO_2$ sensor being the same or different as the ion selective electrode comprising said pH sensor; and an analyzer, wherein the analyzer is configured to correct a measurement of the first ion selective electrode sensor based upon the measured conductivity and temperature, and wherein the analyzer is configured to correct a measurement of the chlorine sensor based upon the measured pH.

17. The apparatus of claim 16, wherein the analyzer is configured to correct a measurement of the second ion selective electrode sensor based upon the measured conductivity and temperature.

18. The apparatus of claim 17, wherein the analyzer is configured to correct a measurement of the pH sensor based upon measurements of the first and second ion selective electrode sensors and based upon the measured temperature.

* * * * *

UNITED STATES PATENT AND TRADEMARK OFFICE
CERTIFICATE OF CORRECTION

PATENT NO. : 7,189,314 B1 Page 1 of 1
APPLICATION NO. : 10/657760
DATED : March 13, 2007
INVENTOR(S) : Salvatore J. Pace et al.

It is certified that error appears in the above-identified patent and that said Letters Patent is hereby corrected as shown below:

In the Claims:

At Column 16, line 57, "substrate; and" should be -- substrate and --.

Signed and Sealed this

Twenty-third Day of October, 2007

JON W. DUDAS
*Director of the United States Patent and Trademark Office*